United States Patent
Roques

(10) Patent No.: US 7,513,936 B2
(45) Date of Patent: Apr. 7, 2009

(54) FLAT SPIRAL CAPILLARY COLUMN ASSEMBLY WITH THERMAL MODULATOR

(76) Inventor: Ned J. Roques, 152 S. Foster Dr., #20, Baton Rouge, LA (US) 70806

( * ) Notice: Subject to any disclaimer, the term of this patent is extended or adjusted under 35 U.S.C. 154(b) by 175 days.

(21) Appl. No.: 11/417,611

(22) Filed: May 3, 2006

(65) Prior Publication Data

US 2006/0283324 A1    Dec. 21, 2006

Related U.S. Application Data

(60) Provisional application No. 60/677,665, filed on May 3, 2005.

(51) Int. Cl.
*B01D 53/02* (2006.01)
(52) U.S. Cl. ............... 96/101; 73/23.39; 95/87
(58) Field of Classification Search ............ 95/82, 95/87; 96/101, 102, 103, 104; 73/23.25, 73/23.35, 23.36, 23.39, 23.42
See application file for complete search history.

(56) References Cited

U.S. PATENT DOCUMENTS

| | | | | |
|---|---|---|---|---|
| 3,149,941 A | * | 9/1964 | Barnitz et al. | 96/101 |
| 3,538,744 A | * | 11/1970 | Karasek | 73/23.39 |
| 4,038,055 A | * | 7/1977 | Varano et al. | 96/102 |
| 5,105,652 A | * | 4/1992 | Manfredi et al. | 73/23.25 |
| 5,132,012 A | * | 7/1992 | Miura et al. | 210/198.2 |
| 5,236,668 A | * | 8/1993 | Higdon | 422/89 |
| 5,298,225 A | * | 3/1994 | Higdon | 422/89 |
| 5,856,616 A | * | 1/1999 | Maswadeh et al. | 73/23.42 |
| 5,979,221 A | * | 11/1999 | Walte et al. | 73/23.25 |
| 5,983,703 A | * | 11/1999 | Wylie et al. | 73/23.42 |
| 6,217,829 B1 | * | 4/2001 | Mustacich et al. | 422/89 |
| 6,296,685 B1 | * | 10/2001 | Cammann et al. | 95/45 |
| 6,454,840 B1 | * | 9/2002 | Gellert et al. | 96/101 |
| 6,527,890 B1 | * | 3/2003 | Briscoe et al. | 156/89.11 |
| 6,699,392 B1 | * | 3/2004 | Manginell et al. | 210/656 |
| 6,732,567 B2 | * | 5/2004 | Briscoe et al. | 73/23.39 |
| 7,343,779 B1 | * | 3/2008 | Yu | 73/23.41 |

* cited by examiner

*Primary Examiner*—Duane S Smith
*Assistant Examiner*—Robert A Clemente
(74) *Attorney, Agent, or Firm*—Phelps Dunbar

(57) ABSTRACT

The gas chromatography (GC) column assembly described herein consists of capillary GC column material, such as fused silica or metal capillary tubing, which is constrained to lie in a flat, ordered, spiral pattern and then encased between two thin opposing surfaces. The resulting column assembly is flat, dimensionally stable and can be very efficiently thermally modulated. The resulting column assembly also takes up very little space, has very little thermal mass, and can be easily and accurately manufactured. The column assembly can be adapted for chromatographic use by affixing it to the surface of a thermal modulator described herein by means of adhesive force or by mechanical compression, and then by attaching the free ends of the exposed column material to the input and output ports of the chromatographic device.

3 Claims, 15 Drawing Sheets

FLAT SPIRAL CAPILLARY COLUMN ASSEMBLY WITH THERMAL MODULATOR

This application claims the benefit of U.S. Provisional Application No. 60/677665 filed May 3, 2005.

BACKGROUND OF THE INVENTION

1. Field of the Invention

The invention contained herein pertains to the field of gas chromatography and more specifically to compact capillary column assemblies and the thermal modulators used to modulate the temperature of the compact capillary column assemblies in order for chemical compounds to be optimally separated from one another. The invention is primarily concerned with thermally efficient, compact, dimensionally flat, rugged, low thermal mass capillary column assemblies of varying flat geometries and the attachment of such capillary column assemblies to various types of thermal modulators for integration with a wide variety of currently available gas chromatographic devices. It is the ultimate goal of this invention to provide the field of gas chromatography with a device that is extremely compact, consumes the smallest amount of power possible, can be efficiently and accurately reproduced and yet can still extract the maximum amount of theoretical separation efficiency from the capillary column material.

2. Prior Art

In the field of gas chromatography a chemical sample is physically placed into the injection port of a gas chromatograph (GC). The injection port is usually at an elevated temperature such that the chemical sample, if not already in the gas phase, becomes immediately vaporized. A stream of continuously flowing gas, referred to in the field as carrier gas (mobile phase), sweeps the vaporized chemical sample into a chromatographic separation column, which, in most state-of-the-art high resolution chromatographic devices, consists of a hollow tube that can vary in length from mere tens of centimeters to hundreds of meters in length. The inside diameter of such tubes can also range in size from 25 micrometers up to 530 micrometers and are generally produced from fused silica, coated with a layer of high temperature polyimide or from long sections of metal capillary tubing. Evenly coated on the inner surface of the separation column is a thin layer of viscous or polymeric material with specific chemical properties that are chosen to interact with the chemical sample previously swept inside by the carrier gas. This type of separation column is generally referred to as a capillary chromatographic separation column or capillary column for short and can be obtained in bulk lengths from several different manufacturers such as Agilent Technologies, Varian/Chrompack, Restek, Supelco, SGE, VICI and Quadrex.

The "heart" of any chromatographic device is its separation column. The separation column operates through the interaction of the thin layer of material coated on its inner surface and the vaporized chemical sample placed inside one end of the separation column by the carrier gas. As the carrier gas and chemical sample progress down the length of the separation column, the individual chemical compounds contained in the sample interact at different rates with the coating on the inner surface of the tube. These interactions between the different compounds contained in the chemical sample and the inner surface of the tube effectively reduces the speed at which each compound traverses the length of the separation column. Dependent upon to what degree each chemical compound interacts with the material coating on the inner surface of the separation column, the overall effect is that each chemical compound becomes spaced in time from one another and ultimately exits the end of the separation column, opposite the injection end, in discrete "bands" ideally containing only one chemical compound. The discrete "bands" exiting the separation column are then channeled to a detection device which determines at frequent, regular intervals of time, how much chemical sample is present and with certain classes of detection devices, what type of chemical is present also.

The amount of time required for a chemical compound to traverse the entire length of a separation column is known as its retention time. In high performance capillary gas chromatography four major factors contribute to the retention times of chemical compounds: separation column length, chemical composition of the coating on the inner surface of the separation column (stationary phase), linear carrier gas velocity, and most significantly, the temperature of the separation column. Well known in the field is the fact that for a given separation column length and stationary phase coating, there exists an optimal linear carrier gas velocity and separation column temperature where individual chemical compounds pass through the separation column and are separated from similar chemical compounds most efficiently. This optimal set of conditions is only effective for a narrow range of chemical compounds and any compounds that exist outside of this narrow range may not separate from one another or may exit from the separation column very slowly if at all. This proved to be very limiting if a chemical sample to be analyzed contained compounds with a broad boiling point distribution. Fortunately, it was discovered that by increasing the temperature of the separation column while the chemical compounds were traveling down the length of the separation column, in effect, the optimal conditions "window" could be moved in time such that at least a portion of the time each chemical compound spent in the separation column was under optimal conditions. This discovery greatly increased the range of chemical compounds that could be efficiently separated in a single analysis cycle and quickly expanded the use of gas chromatographs.

The method of changing the temperature of the separation column while the chemical sample progresses down the length of the separation column is referred to as temperature programmed gas chromatography. The faster the separation column is temperature programmed, the faster a single analysis cycle can be completed thus increasing the number of chemical samples that can be analyzed in a given length of time. In order to increase the temperature of the separation column in a precise manner the chromatographic device must contain a controlled thermal region to house the separation column. In conventional gas chromatographs this is accomplished by incorporating a convection oven large enough to house the capillary separation column which is usually coiled on a round wire rack approximately six inches in diameter. The wire rack containing the separation column hangs freely in the oven with the open ends connected to the injector and detector ports which protrude through the walls of the oven box. The air contained inside the oven is heated by wire filaments and is circulated with a fan located inside the oven in order to maintain a constant, even temperature distribution throughout the entire oven volume. Thermal energy from the heated air is then used to heat the relatively insignificant thermal mass of the separation column. This results in very even heating of the separation column along its entire length and consequently produces very efficient chromatographic performance, but at a significant cost. The amount of power required to heat the oven volume to a normal upper temperature limit of approximately 350 to 400 degrees C. is on the order of single digit kilowatts with a heating rate limit usually around 90 degrees C./minute, when in contrast, the amount of power required to heat the separation column material only is orders of magnitude less. Much energy is wasted. Because of the large amount of power being consumed to heat the oven, large amounts of insulation must be employed to contain the heat, consequently, the bulky nature of conventional gas chromatographs can be directly attributed to the oven/insulation combination. Due to the large amount of power and space required to thermally modulate and house the capillary separation column when coiled on a conventional wire rack, this design is impractical for use in miniaturized or portable/transportable gas chromatographic systems. Several successful attempts have been made at reducing the separation column wire rack size and the ovens that contain them. While power consumption was reduced, these gas chromatographs still consume relatively large amounts of power, on the order of a kilowatt, and are mostly confined to isothermal oven operation or very slow temperature programming rates with limited upper temperatures when being used in a transportable mode where power supply is a relevant issue. This severely limits the range of compounds that can be analyzed as well as increases the amount of time necessary for each analytical cycle. It became quickly apparent that if temperature programmed gas chromatographs were to become smaller, faster and less demanding of power, which are desired traits in nearly all cases, a more energy efficient method of thermally modulating the separation column was going to be needed.

One solution to this problem is to transfer thermal energy directly to the surface of the separation column rather than heating the air surrounding it and having the air transfer the thermal energy. Sides, et al. in U.S. Pat. No. 5,014,541 describe a miniaturized separation column assembly that replaces the traditional column oven in which a separation column is wound directly onto a tubular heat conducting support that contains a resistance heating element. This heating element is temperature programmed to provide the necessary thermal energy for the separation column. While this development reduced the size of the gas chromatograph, the power consumption continues to remain high at around 1 kW.

A different method of thermally modulating capillary separation columns arose in response to the need for reduced size and power consumption gas chromatographs. This method entails the coupling of thermally modulating elements, temperature sensing elements and capillary column material as a single unit. Once such method is described in U.S. Pat. No. 5,005,399 where a thin conductive film is deposited on the surface of a fused silica capillary column which is then wound onto an insulating support structure. A current is passed through the conductive film in order to thermally modulate the length of capillary column. This technique provided for a large reduction in power consumption versus convection oven designs but suffers from inconsistencies in the thin conductive film thickness, as well as damage to the thin conductive film during handling, coiling and heating/cooling cycles. These inconsistencies in film thickness along with damaged portions of the conduction film act to create variances in the resistance across the length of the capillary column which, when current is passed through the conductive film, causes localized hot spots to form on the capillary column surface. A very negative consequence of these hot spots is a non-uniform distribution of thermal energy across the length of the capillary column and ultimately an overall reduction in the chromatographic separating efficiency of the capillary column material. Also, when larger currents are passed through the thin conductive film to achieve faster temperature programming rates or to maintain the capillary column at higher temperatures, the localized hot spots begin to hasten the degradation of the thin conducting film which eventually leads to a failure of the heating system. In addition, the degree to which the capillary column can be compactly contained is limited by the insulation needed to protect successive coils from electrical short circuits, especially at higher temperatures above 200 degrees C., and the minimum bend radius that the thin conductive film can withstand before breakage occurs. This limitation usually results in a cylinder shaped arrangement of coils with a minimum radius of approximately 7.5 cm and cylinder height dependent on the length of capillary column needed. The final size of this column assembly quickly approaches that of a conventional wire-rack wound capillary column previously mentioned. Yet another drawback to using this method to thermally modulate the capillary column stems from the fact that the deposition of thin conductive films to the surface of fused silica capillary column material requires an intricate, detailed process that further complicates the manufacturing of the capillary column, thus severely limiting the variety of capillary column types available and manufactures willing to produce them. In the end, the use of thin film resistively heated capillary columns has major shortcomings when applied to the development of low power, small, fast gas chromatographs.

A second approach to the coupling of the capillary separation column, thermally modulating element, and temperature sensing element was developed by Roundbehler, et al. of Thermedics Detection Inc. in U.S. Pat. No. 5,808,178. This technique, which is marketed and sold under the trade names "FlashGC" and "EZ-Flash", consists of a capillary separation column inserted into a conducting sheath (a metal tube in the commercially available version) or by direct resistive heating of a metal capillary separation column where the metal sheath or capillary column also operates as a resistance temperature detection device. While this technique solves the problem associated with the thin resistive film breakdown and hot spots of the previously discussed technique and consequently produces even thermal distribution across the length of the capillary column, the problem of having to electrically isolate successive coils from one another continues to limit the overall compactness of the design. Additionally, the extra thermal mass contributed by the resistively heated metal sheath in which the capillary column is placed, dramatically increases the power consumption of the device. It is stated in their patent that "a power supply capable of delivering up to 96 Volts at 12 Amps provides sufficient power to heat the tube (metal sheath) to desired temperatures" which is on the order of approximately 1 kW and approaching conventional convection oven power requirements, once again making it an impractical choice for the miniaturization of temperature programmed gas chromatographs.

Overton, et al. describe a miniaturized gas chromatograph in U.S. Pat. No. 5,611,846 which is sold by Analytical Specialists Inc. (ASI) under the trade name "microFAST GC" and uses a similar technique for thermal modulation of the capillary column as that of the previously discussed design. Instead of a metal sheath or metal capillary column used as the resistive heating element, a technique is described whereby a resistively heated wire is placed inside a small insulating sheath. This sheathed heater wire is then bundled in a parallel fashion with a low thermal mass, high resistance temperature sensing wire and a capillary separation column. The entire bundle is then placed inside a second insulating sheath and finally coiled onto an insulated support structure in a helix type geometry. The main advantage of this design lies primarily in the use of a wire arranged directly adjacent to and parallel with the separation column versus a relatively bulky metal sheath in which the capillary column is housed. The overall thermal mass of the assembly is considerably reduced which results in lowered power consumption and cool down times. This reduced level of power consumption allows for short 1-2 meter separation column assemblies to be practically implemented in a miniaturized gas chromatograph that is small, fast and relatively low in power consumption such as the "microFAST GC". However, due to the extra steps involved with inserting the heater wire into a length of insulating sheath and then inserting the bundle of capillary column material, fragile sensor wire, and sheathed heater wire into a second insulating sheath, it becomes a very tedious, nearly impractical exercise to manufacture a separation column assembly in this manner any longer than 3 meters. This limitation in column length reduces the range of chemicals that can be separated in a single analysis and, while the power consumption is greatly reduced when compared to a conventional GC oven, in reality the column assembly still consumes enough power to prevent its use in truly portable, battery operated, temperature programmable GC designs.

In response to these shortcomings, Mustacich, et al., in U.S. Pat. No. 6,217,829, describe a reduced power consumption capillary separation column assembly that, in order to conserve energy, relies on a tightly packed geometry containing a resistively heated element, temperature sensing element and capillary separation column. The assembly is constructed by bundling all three elements in a parallel fashion then coiling the entire bundle into a tightly packed torus shaped geometry. The assembly is then wrapped in a thin layer of metal foil to prevent the assembly from uncoiling. The end result is a very low thermal mass, compact separation column assembly that can be rapidly heated and cooled. Claimed power consumption data is on the order of single digit Watts for temperature programming rates ranging from 1 to 10 degrees C./s to a final temperature of 180 degrees C. using capillary column lengths on the order of 1 meter. No mention is made of power consumption data for higher final temperature values or for longer separation column assemblies. Besides the complexity of manufacturing such an assembly, one drawback that this design presents deals with the round cross-sectional nature of a tightly packed, randomly arranged series of elements in a toroidal geometry. When the resistive element begins to heat the assembly, a temperature gradient almost immediately forms between the outer foil wrapped surface and the center of the cross-sectional area due to insulating effects that the outer coils have on the inner most coils. Because of the randomly arranged coils within the torus geometry, this results in uneven heating across the entire length of the capillary column and as a consequence, a reduction in the chromatographic separating efficiency of the capillary column material.

Capillary column separation assemblies that contain a thermally modulating element, a temperature sensing element and a capillary column as a single unit for integration with a gas chromatograph, as discussed in the preceding paragraphs, present another set of problems not yet discussed. In a conventional gas chromatograph where a convection oven is used to heat the capillary column, the oven is a permanent part of the device. Because of the numerous variables involved in the temperature feedback control system of the oven (e.g. variations in temperature sensing elements, variations in control electronics, variations in overall device calibration etc.), each gas chromatograph oven has its own unique heating characteristic or signature. When a capillary column needs to be replaced in a conventional GC the only factor affecting the performance of the device once the new capillary column is installed, is the new capillary column itself, not the GC oven since it remains a permanent part of the system. And, since capillary column manufacturing has become a nearly perfected art, the variations are usually small. However, with the capillary column assemblies that contain the thermally modulating element, temperature sensing element and capillary column as one unit, the entire oven and capillary column are being replaced at the same time therefore introducing a different heating characteristic to the overall system. Depending on the type of chemical analysis being performed, this could result in unacceptable performance variations after a capillary column assembly change is made. A second general problem associated with the various "single unit" capillary column assembly designs deals with the extra manufacturing burden generated from having to couple all of the various elements into a precise orientation and then the extra steps involved attaching them to insulated support structures and electrical lead connections. This usually involves having a person with expert technical skill make the column assemblies and ultimately a much higher end cost to the consumer.

Another technique that has been developed to thermally modulate a capillary separation column that claims low power consumption and compact design, uses microwave energy as its heating source and is described by Gaisford, et al. in U.S. Pat. No. 6,316,759. This technique involves the use of highly specialized resonant microwave cavities, a microwave source, a waveguide for channeling the microwaves to the resonant cavity and capillary columns specially coated with microwave absorbing material. While this technique may result in a minimal amount of power being needed to thermally modulate the separation column in a fairly compact form, the amount of specialized hardware necessary to perform this function make it an expensive, impractical choice for use in miniaturized portable/transportable temperature programmed gas chromatographs where ruggedness and simplicity of design are better suited.

One such example of a proposed rugged and simple design is described by Walte, et al. in U.S. Pat. No. 5,979,221. This design describes the use of an infra-red (IR) heat lamp as a heat source in which the heat lamp is positioned as a lid to an insulated open cavity. At the bottom or along the walls of this cavity resides either a cylindrical or flat spiraled capillary separation column. The heat lamp is not placed in intimate contact with the column assembly but rather heats by radiating thermal energy from a distance. This is most likely done in order to provide a more even thermal energy distribution from the heat lamp to the surface of the capillary separation column, however, this results in a much larger than necessary power requirement to heat the device. While there is nothing new and innovative about coiling a long thin object into a flat spiral, it is by no means a trivial task, due to the elastic, "springy" nature of capillary separation columns, to confine a length of capillary column material to a flat, spiraled orientation in which the final assembly is rugged and can withstand repeated exposure to temperatures above 300 degrees C. without structural failure. No mention is made in their description as to how such a rugged, flat, spiraled capillary column assembly could be constructed nor is there any mention of the chromatographic separating efficiency that could be obtained from the heat lamp/flat spiraled column combination.

SUMMARY OF THE INVENTION

A gas chromatography capillary separation column assembly is provided which contains a capillary separation column or columns of a predetermined length to contain a chemical sample for separation, a thermal modulator to alter the temperature of the capillary separation column assembly and a temperature sensing mechanism used for feedback temperature control of the thermal modulator. Also provided is a means to insulate the capillary column assembly from ambient temperatures.

It is a fundamental object of this invention to provide a gas chromatography capillary separation column assembly which is planar in nature, compact, low in thermal mass, heats evenly and efficiently across its entire surface area, requires relatively little power to heat and cool, and can be easily and accurately manufactured.

It is also a fundamental object of this invention to provide a means for efficiently constructing such a capillary separation column assembly which is also rugged and can withstand repeated exposure to high temperatures without structural failure.

Yet another fundamental object of this invention is to provide a thermal modulating device to which the capillary separation column assembly is attached and contains a temperature sensing mechanism for providing very responsive thermal modulation to the capillary separation column assembly.

It is an object of this invention to provide a capillary column assembly which contains commercially available, standard, fused silica or metal capillary separation columns. The capillary column assembly is constrained to lie in a planar configuration and is perfectly flat on one side. The capillary column material is coiled into a compact spiral form and can have an overall variable shape that is limited only by the minimum bend radius of the capillary column material. More than one length of capillary column material may be coiled simultaneously and may have substantially different stationary phases and diameter dimensions. The compact, spiraled capillary column material is prevented from uncoiling and is protected by encapsulating it through adhesion of two thin opposing surfaces. The thin opposing surfaces can both be flexible in nature or a combination of one flexible surface and one rigid surface. One of the thin opposing surfaces must contain an adhesive material which acts to secure the capillary column material during the spiraling process. The thin opposing surfaces must be made of a material that can withstand repeated exposure to the range of temperatures required for a given chemical analysis. The flexible materials may include, but are not limited to, thin fiberglass cloth, thin ceramic cloth, metal foil, thin polyimide sheet and thin Teflon sheet. Rigid materials may include, but are not limited to, thin metal sheets, thin ceramic sheets, thin polyimide sheets, thin fiberglass boards and thin glass sheets.

It is a further object of this invention to provide a capillary column assembly whose overall surface area consumption is determined only by the minimum bend radius of the capillary column material, the outside diameter of the capillary column material and the desired capillary column length to be coiled. This allows for ultra-compact, very low thermal mass capillary column assemblies to be constructed which can consume less surface area than a U.S. quarter and contain approximately 1.5 meters of capillary column length. This is ideal for use in battery operated portable temperature programmed gas chromatographs where space and available power are at a minimum. At the other extreme, this allows for capillary column assemblies containing very long lengths of column material (30 meters and above) to also be constructed while maintaining a very compact planar form.

It is still a further object of this invention to provide a capillary column assembly which, due to the perfectly flat, ordered, compact nature of the spiraled coils of capillary column material contained in the column assembly, can be very efficiently and evenly heated/cooled across the entire length of the capillary column when placed in intimate contact with a flat thermal modulator. This efficient, even application of thermal energy to the capillary column assembly is essential for extracting the maximum separating capability from the capillary column material itself while using a minimum amount of power to do so. This efficiency also allows for fast thermal modulation of the capillary column assembly which is ideal for fast gas chromatography where short analysis times are the primary objective.

It is still a further object of this invention to provide a capillary column assembly that is multi-sectioned and contains one continuous length or lengths of capillary column material with each section capable of being independently thermally modulated. This is useful in situations where a chemical sample needs to be pre-concentrated before being separated. One section of the column assembly can be designed to function as a reduced temperature zone for capturing and concentrating sample which is later rapidly heated to transfer the concentrated chemical sample to the next zone for further sample processing or for separation.

It is yet a further object of this invention to provide a capillary column assembly that is adhesively bonded to a flat thermal modulator to provide intimate contact. Also provided is a capillary column assembly that remains separate and not adhesively bound to the flat thermal modulator but rather is kept in intimate contact with the thermal modulator through the use of even mechanical force. This mechanical force can be applied by a piece of non-conducting compressible material, preferably high temperature insulating material such as polyimide foam, being "sandwiched" between a rigid plate and the surface of the thermal modulator. Pressure can be applied to the rigid plate with the use of devices such as screws, springs or by a hinge and latch. By keeping the thermal modulator separate and unbound from the capillary column assembly, the thermal modulator can remain as a permanent part of the gas chromatograph thereby preserving its own heating signature and significantly decreasing the likelihood that the end user will have to spend time re-calibrating the instrument. Also, a separate column assembly requires much fewer parts and requires less technical skill and time to construct than a capillary column assembly that contains a thermal modulator, temperature sensing element and capillary column material as one unit. Ultimately this results in a much lower manufacturing cost and end cost to the user.

It is an object of this invention to also provide a capillary column assembly that is adhesively or mechanically attached to a thermal modulator that is comprised of a flat, thin low thermal mass surface. The thermal modulator surface can be a non-conducting material such as mica, or ceramic. A non-conducting thermal modulator can be constructed with a resistive heating element that matches the size and shape of the portion of the capillary column assembly that contains only the capillary column material. In this manner heat is only applied to the capillary column material itself and not the empty inner circle or outer perimeter of the capillary column assembly. This accounts for a further reduction in power consumption, especially when larger length capillary column assemblies are employed. It should be noted that for a thermal modulator designed to heat a given length of capillary column material, the same thermal modulator can also heat capillary separation column assemblies containing shorter lengths of column material provided that the body of the column material is constrained to lie within the bounds of the heated area on the surface of the thermal modulator. This creates a versatile "one size fits all" type configuration for capillary separation column assemblies up to the maximum size that the thermal modulator can accommodate. A thin layer of thermally conductive material such as aluminum or copper foil in the shape of the compact capillary column body contained within the capillary column assembly may be deployed between the shaped heater element and the capillary material in order to smooth out any temperature fluctuations that may exist across the heater element. This provides for an exceptionally even transfer of thermal energy to the capillary column material which is necessary for maximally efficient chemical separations. For ultra-compact capillary column assemblies that have a very small overall area it may be more mechanically convenient to heat the entire thermal modulator surface rather than just the area containing the capillary column material. This can be accomplished by designing a heater element to cover the entire surface to which the capillary column is attached. A layer of conducting material once again can be employed between the thermal modulator surface and the capillary column material in order to smooth out temperature fluctuations.

It is further an object of this invention to provide a capillary column assembly that is adhesively or mechanically attached to a thermal modulator that contains a resistive heating element that is an elongated resistive heater wire woven into the surface of the non-conducting thermal modulator flat surface material. More conveniently, the heater element can be a thin, flat, resistive element chemically etched in the shape and resistance desired from a single sheet of conductive material and then encapsulated on the non-conducting thermal modulator flat surface material with a layer of flexible, non-conducting, low thermal mass, temperature resistive, adhesive coated material such as thin fiberglass or ceramic cloth, thin polyimide sheet or thin Teflon sheet.

It is still further an object of this invention to provide a capillary column assembly that is adhesively or mechanically attached to a thermal modulator that contains a low thermal mass, fast responding, temperature sensing element that is to be used for electronic temperature feedback control of the thermal modulator surface. The temperature sensing element can consist of but not limited to, low thermal mass resistance temperature detection (RTD) wires, pre-made and commercially available RTD elements, thermocouples, and thermistors. The temperature sensing devices can be placed between the thermal modulator surface and the capillary separation column assembly. Alternatively, the resistive heating element can be designed such that a small piece of element trace strays away from the main body of the heater element shape. A discrete temperature sensing element can then be placed on this stray trace without interfering with the continuity of the main heater element body surface where the capillary column assembly must make intimate contact. Temperature feedback control of the thermal modulator is to be generally provided by the gas chromatograph to which it is attached or by any set of commercially available electronic controllers so designed. A discussion of the numerous electronic circuits and algorithms used to perform such temperature controlling functions would be beyond the intent of this invention and are already well known in the art and thus will be omitted, with the exception that it is understood that proper temperature control is a necessary component of performing accurate, repeatable chemical analysis.

It is still further an object of this invention to provide a capillary column assembly that is adhesively or mechanically attached to a thermal modulator that is insulated on both the top and bottom surfaces with a high temperature, highly insulating material such as polyimide foam in order to reduce convective heat losses and therefore reduce the power consumed by the device. Because this would provide a lengthy cool down time in temperature programmed analysis, one face of the thermal modulator surface can be left un-insulated to facilitate faster cooling. Even faster cooling can be achieved with the use of a small fan to force a flow of air across the face of the un-insulated surface.

It is yet still further an object of this invention to provide capillary separation column assemblies that are adhesively or mechanically attached to a multi-sectioned thermal modulator. This multi-sectioned thermal modulator can have multiple heated surface zones attached to the same base in which multiple individual capillary separation column assemblies can be attached or a single multi-sectioned capillary separation column assembly can be attached. This provides a means to thermally modulate the multi-sectioned capillary separation column assemblies described above or to provide a means to thermally modulate multiple individual capillary separation column assemblies independently. The latter is useful in situations where it is necessary to perform "stream-splitting", "backflushing" or "heart-cutting" type chemical analysis operations.

It is still further an object of this invention to provide a capillary column assembly that is adhesively or mechanically attached to a thermal modulator that is a thermoelectric Peltier device. Because of the extremely compact, flat nature of the capillary separation column assemblies described herein, long enough sections of capillary column material can be coiled into a space small enough to fit on the surface of commercially available Peltier devices such that sub-ambient temperature programmed gas chromatography can be performed in a very efficient manner. Peltier devices are now available that can withstand temperatures up to 225 degrees C. This kind of sub-ambient chromatography has traditionally been confined to the laboratory where large refrigeration systems are required and use substantial amounts of power or where large tanks of liquid coolant such as liquid nitrogen and liquid carbon dioxide are used to cool a conventional GC oven containing a wire-rack wound capillary column assembly. With a capillary separation column assembly attached, the Peltier device can operate as a cooling and heating device depending on the direction of current flow applied to the device. Chemical compounds that would routinely be inseparable at ambient temperatures due to low retention factors, can now be separated with the overall temperature of the capillary separation column reduced. With the temperature of the capillary separation column reduced even further, the device can function as a trap for concentrating chemical samples, and then by heating the Peltier device, it can act as a separation column for performing the chemical analysis on the same concentrated sample. This can extend the chemical separating range of capillary separation columns to a significant enough degree that what might normally require two different separation columns to separate a given set of compounds can now be done with one or what might normally require an extra long length of capillary column material to separate a given set of compounds can now be performed on a capillary column a fraction of the length.

DESCRIPTION OF THE PREFERRED EMBODIMENTS

It can be shown that from FIGS. 1-15 a high-efficiency, planar capillary column assembly 15 with an integrated thermal modulator 17 is presented for use with gas chromatographic devices. Such an integrated capillary separation column system is especially beneficial for use in portable/transportable gas chromatographic systems where limited space and power are available yet maximal chromatographic results are needed. Because of its compact nature the capillary column assembly 15 and thermal modulator 17 can together be adapted for use in a wide variety of gas chromatographic devices and should not be limited to a specific class of instruments such as portable/transportable, laboratory or process GC.

Figure 1:
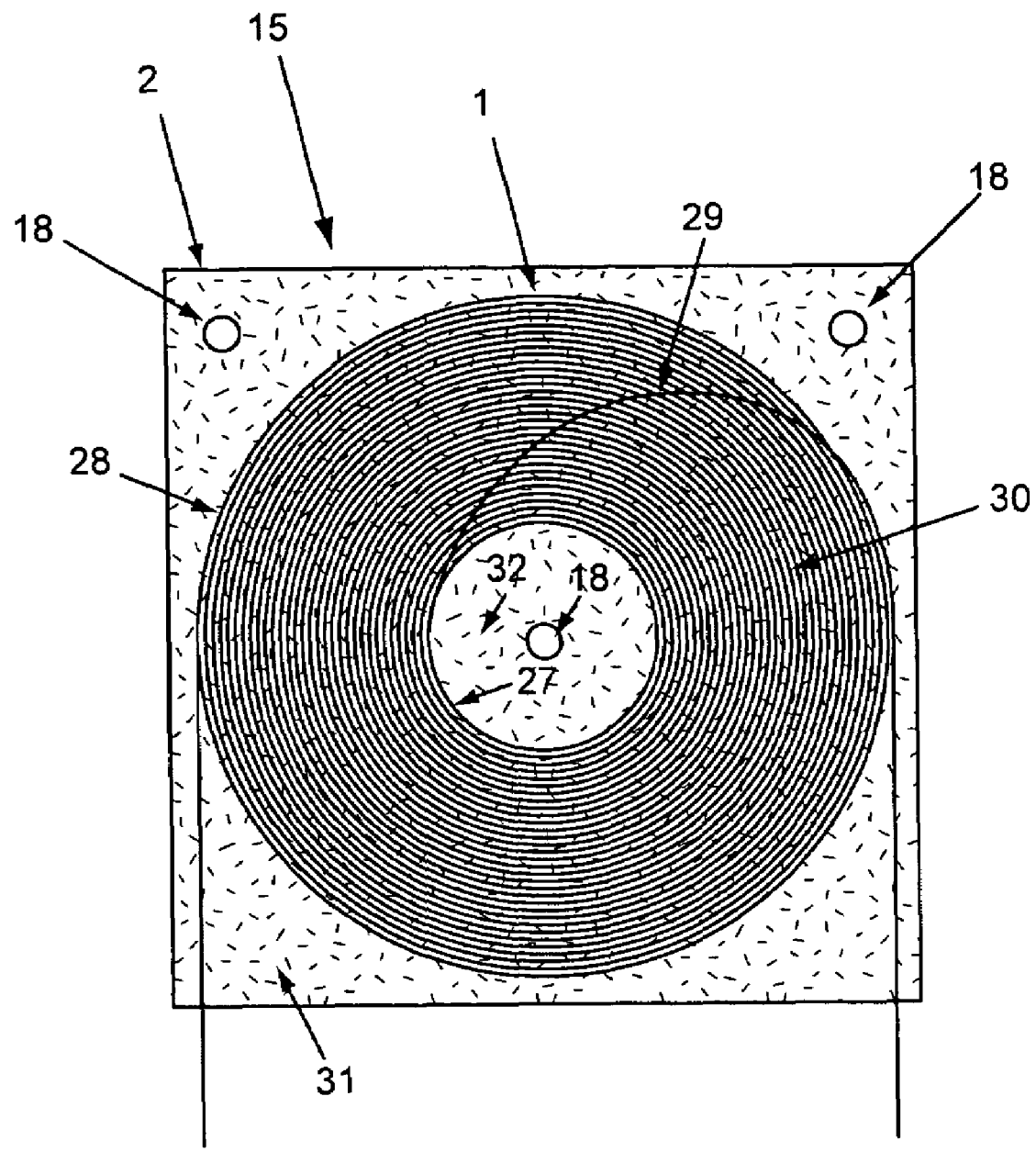
FIG. 1 is a schematic representation of the planar capillary column assembly showing coiled capillary separation column material encapsulated within two thin opposing surfaces.
Figure 2:
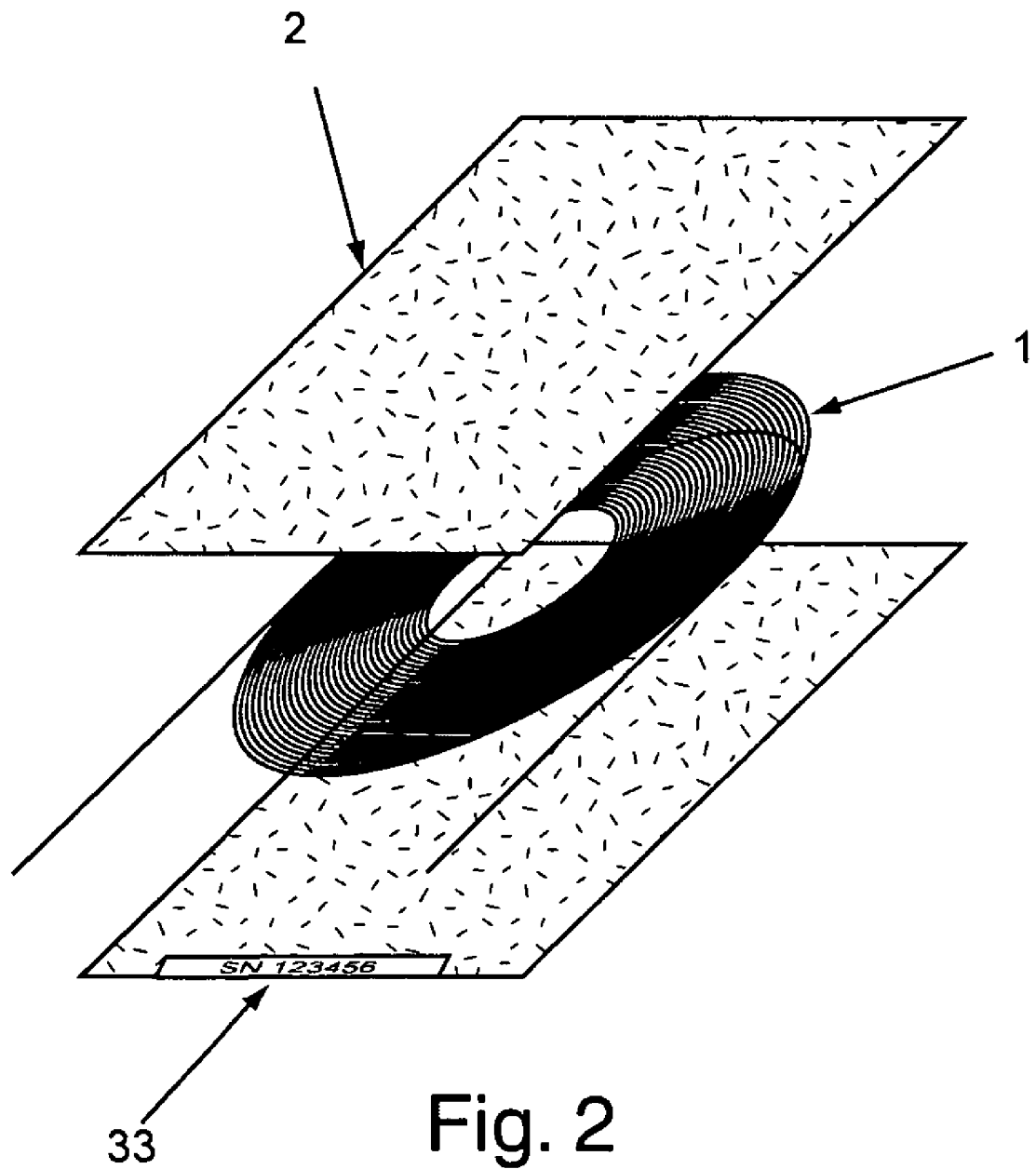
FIG. 2 is a schematic representation of an exploded view of the planar capillary column assembly showing coiled capillary separation column material and two thin opposing surfaces used to encapsulate and constrain coiled capillary separation column material.
Figure 3:
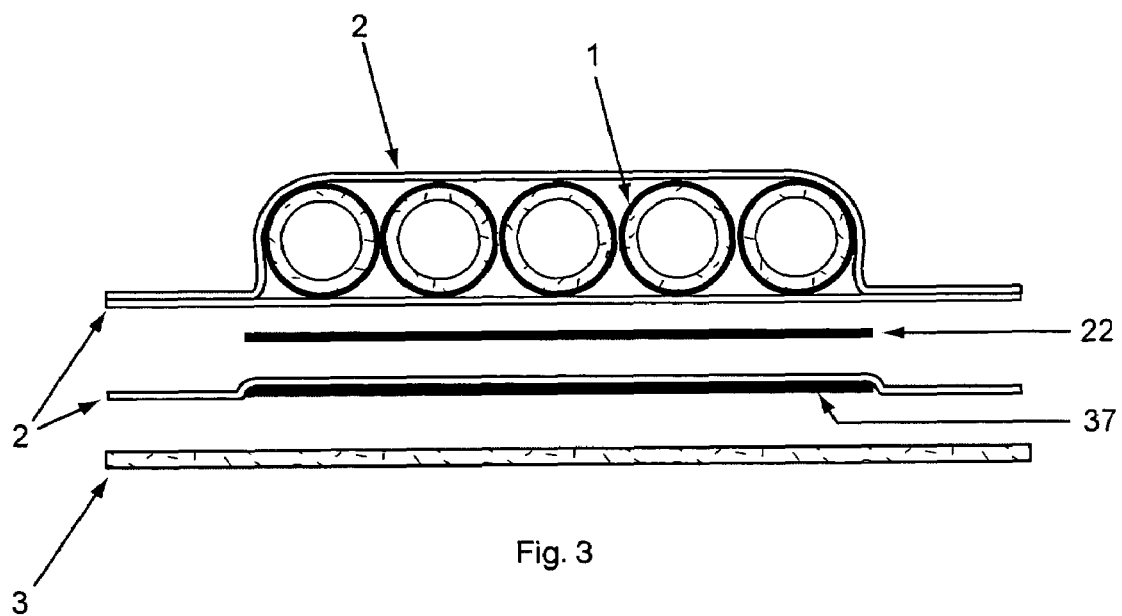
FIG. 3 is a schematic representation of an exploded view of a cross section of the planar capillary column assembly body and thermal modulator surface.
Figure 4:
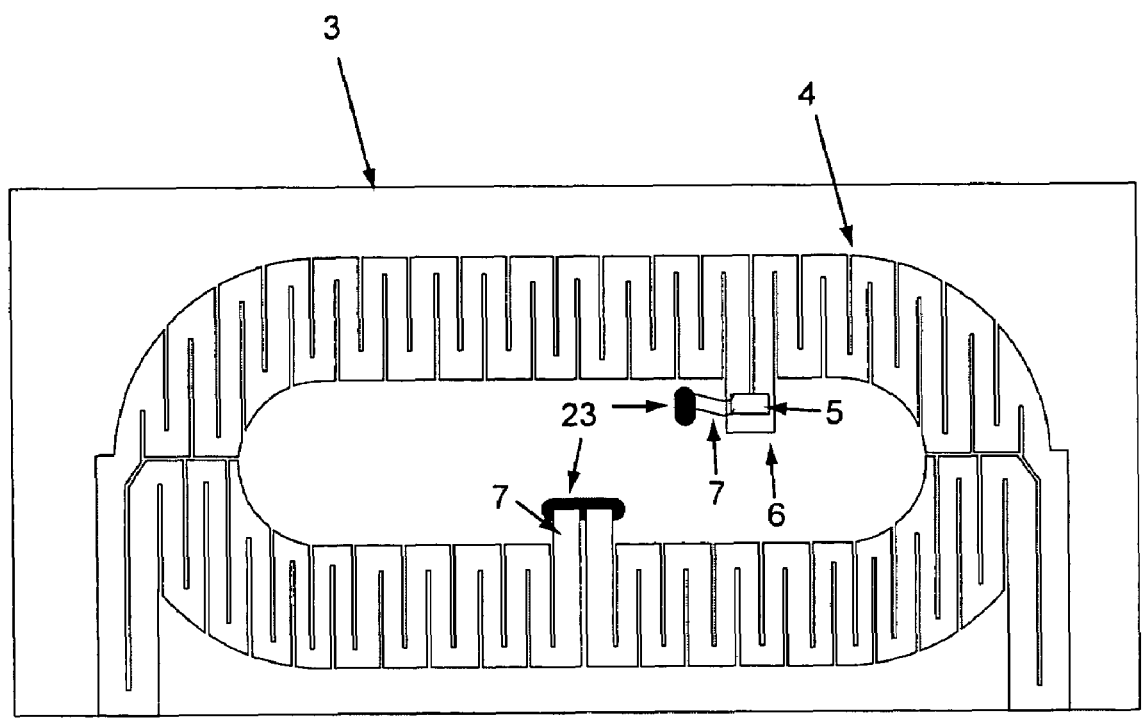
FIG. 4 is a schematic representation of an etched, shaped, resistive heater element shown with stray element trace containing temperature sensing device. The element is positioned on top of thermal modulator surface.
Figure 5:
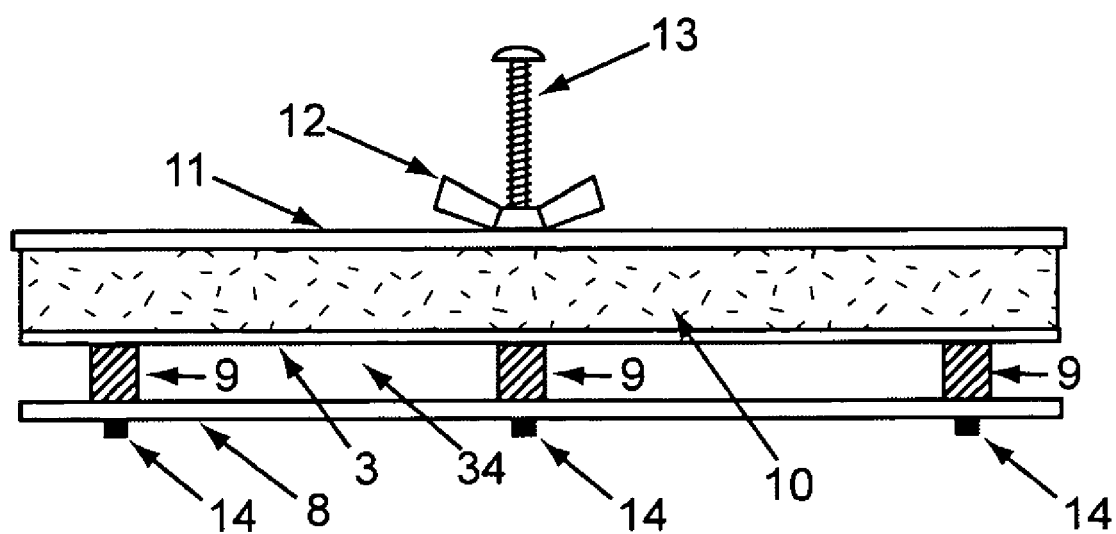
FIG. 5 depicts a capillary column assembly, thermal modulating device installed in a gas chromatograph.
Figure 6:
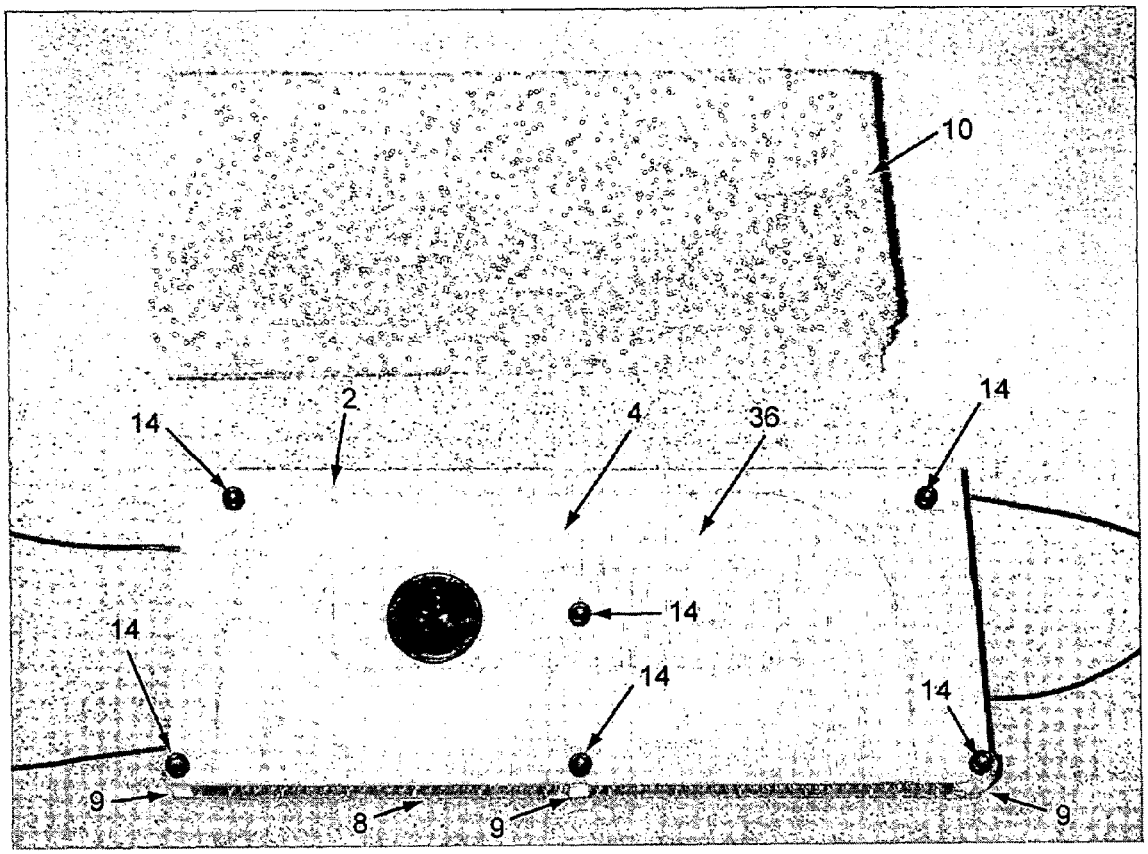
FIG. 6 depicts a capillary column assembly, thermal modulating device without a capillary column assembly attached, therefore exposing the heater surface.
Figure 7:
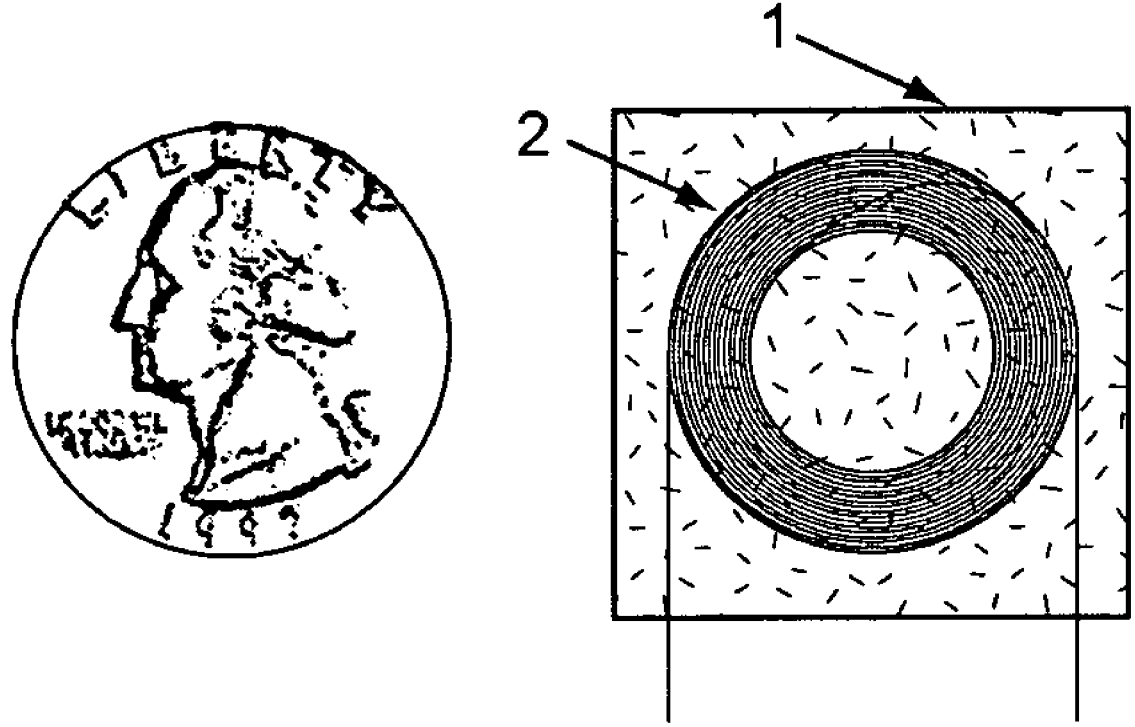
FIG. 7 depicts an ultra-compact capillary column assembly. 1.5 meters of coiled, encapsulated capillary column length of round geometry is shown adjacent to a U.S. quarter for size reference.
Figure 8:
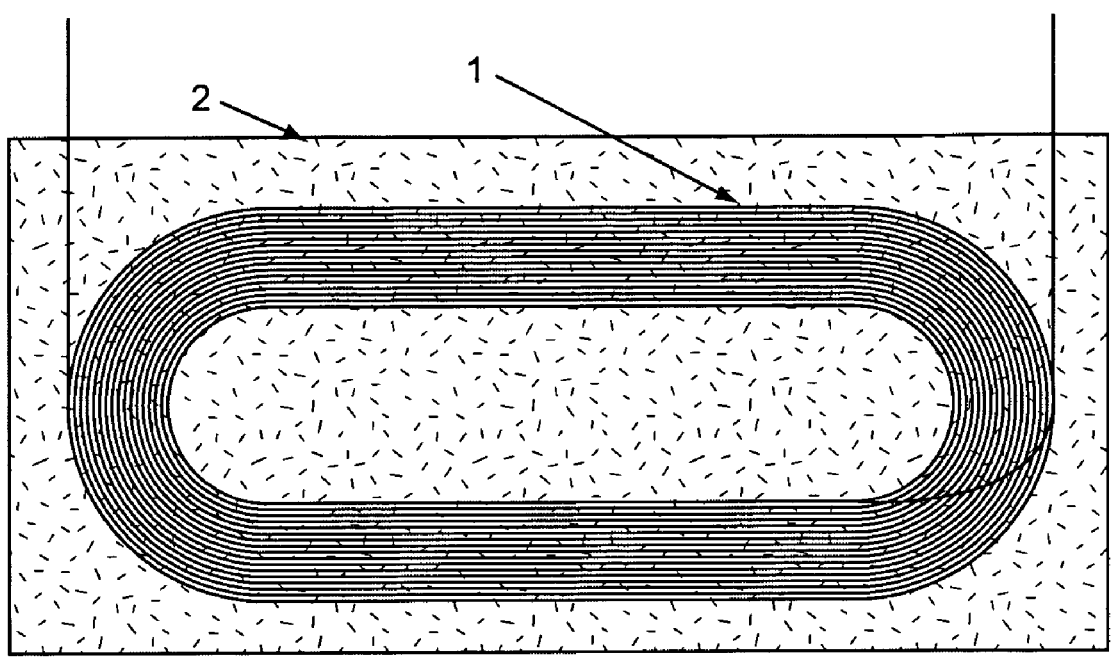
FIG. 8 depicts an oval-shaped, 8 meter in length capillary column assembly before the second thin opposing surface is applied to encapsulate the entire assembly.

The planar capillary column assembly 15 described herein is comprised of a length of capillary column material 1 which can be made of such material as fused silica tubing or metal capillary tubing and is readily, and easily obtainable from several different manufactures such as Agilent Technologies, Varian/Chrompack, Restek, Supelco, SGE, VICI and Quadrex. It is also comprised of two thin opposing surfaces 2, one of which must contain a thin coating of adhesive material to which the capillary column material 1 is affixed during the spiraling process. The thin coating of adhesive material also serves to seal the second thin opposing surface 2 to the first, thereby securely encapsulating the coiled capillary column material 1 between the two thin surfaces 2. The thin opposing surfaces 2 contained in the preferred embodiment consist of a thin, tightly-woven, high-temperature, fiberglass cloth, coated with a thin layer of high-temperature silicone adhesive. The capillary column assembly 15 can be prepared by cutting to a desired shape a section of thin surface material 2 that contains an adhesive coating and then placing the thin surface, adhesive side up, onto a flat working surface. Using a pencil or similar, fine tipped marking device, a pattern is traced directly onto the adhesive surface in the shape of the overall geometry desired for the portion of the capillary column assembly 15 containing the capillary column material 1. As shown in FIG. 1, the pattern traced can represent the innermost shape of the overall capillary column material body 27, whereby coiling of the capillary column material 1 starts in the center and spirals outward. More conveniently, the pattern traced can represent the outermost shape of the overall capillary column material body 28, whereby coiling of the capillary column material 1 starts at the outermost perimeter and spirals inward. The latter approach is particularly useful due to the fact that the previously spiraled outer coil supports the tension created by next inner coil and thus helps prevent a premature unraveling of the capillary column length.

To create the spiraled assembly 15, a length of capillary column material 1 is placed on top of the pattern traced previously and pressed into the adhesive coating of the surface material 2. Once a single revolution of capillary column length is place around, and on top of the pattern traced, the next revolution of capillary column length is placed immediately adjacent to the preceding coil in order to eliminate excess space between successive coils. Spiraling continues in the manner previously outlined until the desired length of capillary column material 1 is coiled or until the minimum bend radius of the material is reached. If the coiling process was initiated from the outer perimeter 28 towards the center, the free end of the column material 29 exiting the center coil of the spiraled column assembly body 30 is placed across the top of the spiraled column assembly body 30 and secured to the thin adhesive coated surface material 2 around the perimeter of the spiraled column assembly body 28 in an orientation that is the most spatially convenient for the input and output ports of the chromatographic device to which the capillary column assembly 15 is to be pneumatically attached. It should be noted that a small length of capillary column material 29 will "cross over" the spiraled column assembly body 30, thus removing it from the plane that makes intimate contact with the thermal modulator 17. However, this length of column material 29 is a very small percentage of the overall capillary column length and is generally only one capillary column diameter removed from the thermal modulator surface 3 and in experimental results it has not been shown to degrade the performance of the device.

When spiraling of the capillary column material is complete, the second thin opposing surface 2 is placed on top of the first thin opposing surface 2 containing the adhesive coating and compressed firmly together to seal the two layers, thereby securely encapsulating the entire coiled capillary column body 30. The excess material contained around the inner and outer perimeter of the sealed capillary column assembly 15 may then be trimmed to the desired shape or holes 18 may be drilled or punched in the encapsulating surface material 2 to coincide with any alignment pins or screw heads 14 that may be present on the thermal modulator device 17. The excess material contained around the inner 31 an outer 32 perimeter of the capillary column body 30 may also contain an identification tag or security device 33 that is encapsulated between the layers of the thin opposing surfaces 2 but not in close enough proximity to the capillary column material 1 as to affect its thermal distribution. Pursuant to the preceding discussion, it is also possible and at times necessary to coil more than one capillary column length into a single capillary column assembly 15. The process is identical to that stated above, with the exception that multiple capillary columns are coiled in tandem onto the adhesive face of the thin surface material 2 rather than just one.

Of the thermal modulators 17 herein discussed, the preferred embodiment is comprised of a thin, rigid, flat, heat resistant surface 3, constructed of a material such as mica or ceramic which is cut in a shape that is ideally suited to the space available for interfacing to a device containing the desired input and output ports to which a capillary column assembly 15 can be pneumatically attached. The heater surface 3 is attached to a rigid base surface 8 by mechanical standoffs 9 to provide an air gap 34 beneath the heater surface 3 and the base surface 8. The air gap 34 is desirable such that air can be circulated near or across the bottom side of the heater surface 3 for fast cooling of both the heater surface 3 and capillary column assembly 15. The base surface 8 may also contain a small fan or fans 35 to facilitate the circulation of air across the bottom side of the heater surface 3. The base surface 8 is preferably a printed circuit board to which temperature sensor 5 and heater elements originating from the heater surface 3 can securely terminate. The heater surface 3 may be attached to the mechanical standoffs 9 with screws or studs 14 that serve also as alignment pins for the capillary column assembly 15. The heater surface 3 may contain holes 23 to allow heater element 4 and temperature sensing element 5 lead wires 7 to protrude through to the base surface 8 for attachment. A resistive heater element 4 is placed in direct contact with the top heater surface 3 and sealed to the heater surface 3 with a thin, non-conducting, low thermal mass, surface material 2 that contains a high temperature adhesive for bonding. The surface material 2 used for bonding the heater element 4 to the heater surface 3 is preferably the same fiberglass material which is used to prepare the capillary column assemblies 15. The resistive heater element 4 is preferably a thin, low thermal mass, shaped, chemically etched, metal filament. The metal filament may be composed of Nickel-Chromium alloys or any other alloys that can withstand high temperatures and provide the volume resistivity characteristics appropriate for the dimensions of the element desired. The resistive heater element may also be composed of a flat, conductive carbon film which can be "sprayed" onto the face of the heater surface 3 in the shape desired with the necessary resistance characteristics. The heater filament 4 may be shaped in such a way so as to provide thermal energy to a specific region 36 of the heater surface 3 containing the coiled capillary column material body 30 and influent and effluent ends 20 of the capillary column material 1, thereby reducing the power consumption of the device. Alternatively, the capillary column assembly 15 may be shaped in such a way as to accept thermal energy from a specific region 36 of the heater surface 3 which contains the shaped heater element 4. Alternatively still, an assortment of capillary column assemblies 15 may be created that contain varying lengths of capillary column material 1 for use with the same thermal modulator 17 provided that the capillary column material body 30 remains within the bounds of the shaped heater element 4. It bears mentioning that it is generally understood in the art that the capillary column material 20 that exists between a capillary column thermal modulating device 17 and the gas chromatograph's pneumatic input and output ports where the column assembly 15 attaches, must be kept sufficiently hot such that "cold spots" do not develop and alter the performance of the overall system. This extra thermal energy is usually provided by the heaters associated with input and output ports of the gas chromatograph and it is not necessarily the intent of this invention to provide for this extra heat. The heater element 4 may contain a stray trace 6 on top of which a temperature sensing element 5 used for temperature feedback control can be attached while not interfering with the intimate thermal contact between the heater surface 3 and the capillary column assembly 15. The temperature sensing element 5 may consist of commercially available platinum RTD elements, thermocouples or thermistors. A thin layer of conductive material such as metal foil 22, may be placed between the encapsulated heater element 37 and the capillary column material 1 in order for minor temperature fluctuations across the heater surface 3 to be equalized, thereby providing a more even temperature distribution to the capillary column material body 30.

The preferred embodiment of this invention also contains a means for providing mechanical attachment of the capillary column assembly 15 to the thermal modulator 17. This means for mechanical attachment is comprised of an elastic, low thermal mass, highly insulating, temperature-resistant material 10 and is preferably commercially available polyimide foam. It is also comprised of a mechanical device to compress the polyimide foam 10 to the surface of the capillary column assembly 15 which is thereby compressed and held in intimate contact with the surface of the thermal modulator 3. This mechanical device may exist as a screw 13 with a compressing nut 12, a spring or a set of springs 24 or a hinged arm 25 with a latch 26. The polyimide compressing foam 10 also serves as insulation for the top face of the thermal modulator 3. This acts to further reduce convective heat losses from the device and consequently reduces overall power consumption. The top face of the polyimide foam 10 opposite the heater surface 3 may also contain a rigid plate 11 to provide even compression of the polyimide foam 10 across the entire surface of the thermal modulator 17. The mechanical compression devices 12, 13, 24, 25, 26 described above may be directly attached to the rigid plate 11 or may be in direct contact with the rigid plate 11 to provide the necessary compressive force to the polyimide foam 10.

Test results were obtained by designing and installing the invention into a "microFAST GC" sold by Analytical Specialists Inc. located in Baton Rouge, La. The GC that was used is of the portable/transportable type and is about the size of a large shoebox. The thermal modulator 17 and capillary column assembly 15 were designed and installed to fit in the available space of approximately 6 inches wide by 3 inches deep by 1.5 inches tall. The available space provided enough surface area to accommodate up to 10 meters of total column length 1. Because the "microFAST GC" contains a dual injector/dual detector configuration, twin capillary column assemblies could be produced up to 5 meters each (for a total length of 10 meters). The onboard electronics of the GC provided the direct temperature feedback control for the thermal modulator 17.

Temperature programmed heating ramps at various rates were performed with the system to observe the power consumption of this specific design. An ammeter was used to record and calculate instantaneous power measurements at various points along the temperature ramps. The results are shown below in Table 1.

TABLE 1

Power Required at 150° C. at Various Ramp Rates

| Heating Rate | Power (Watts) |
|---|---|
| 60° C./min | 21.0 |
| 150° C./min | 50.0 |
| 300° C./min | 91.0 |

The data in this table show that even for very fast temperature programming rates of 300 degrees C./min, the planar capillary column assembly 15 and thermal modulator 17 designed in accordance with this invention, consumes at least a factor of 10 less power, at more than 3 times the ramping rate of most conventional gas chromatographs. Smaller configurations, for instance, designed to hold approximately 2 meters of column material 1 would result in an even further dramatic decrease in power consumption.

Figure 9:
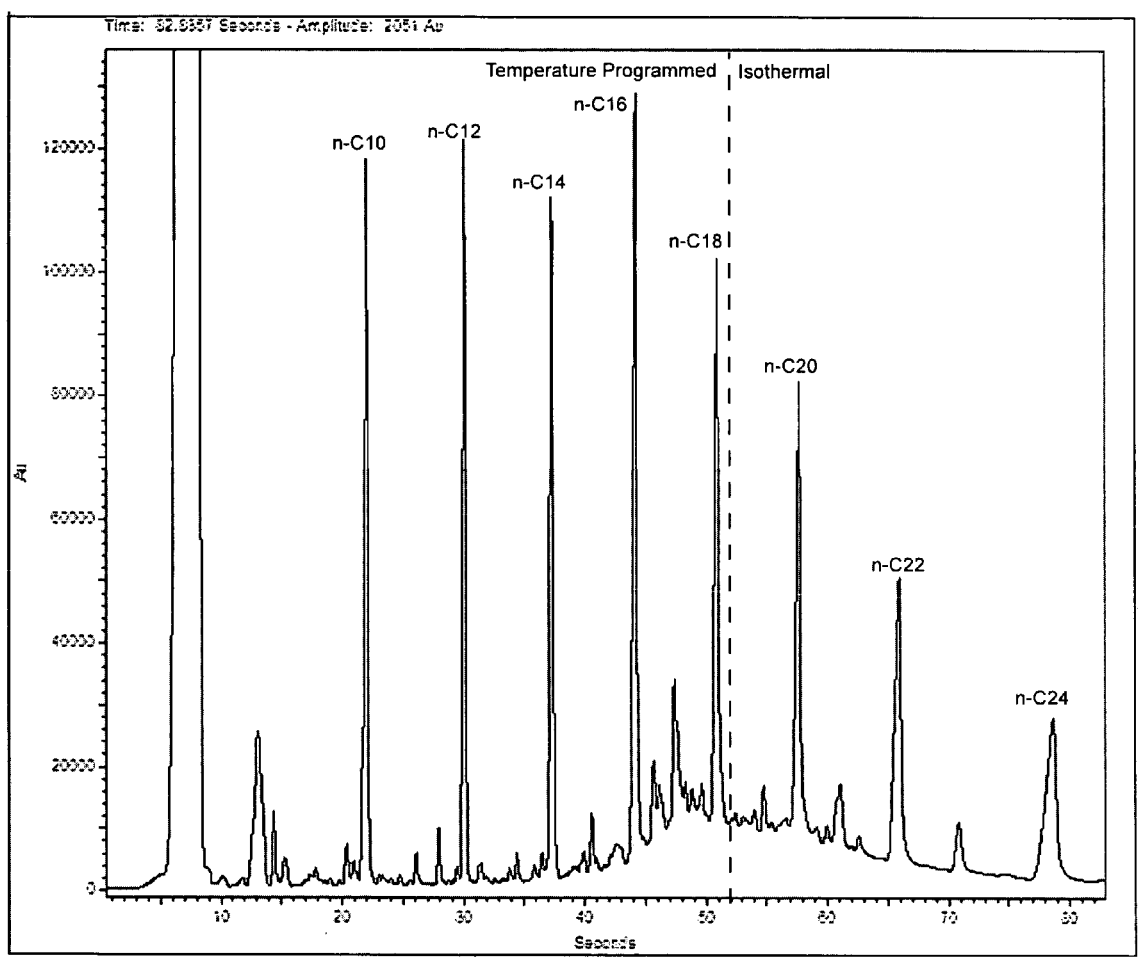
FIG. 9 is a chromatogram showing a fast chemical separation of semi-volatile n-alkane hydrocarbons with a temperature program heating rate of 300 degrees C./minute performed using the subject invention with a 1.7 meter long capillary column length.
Figure 10:
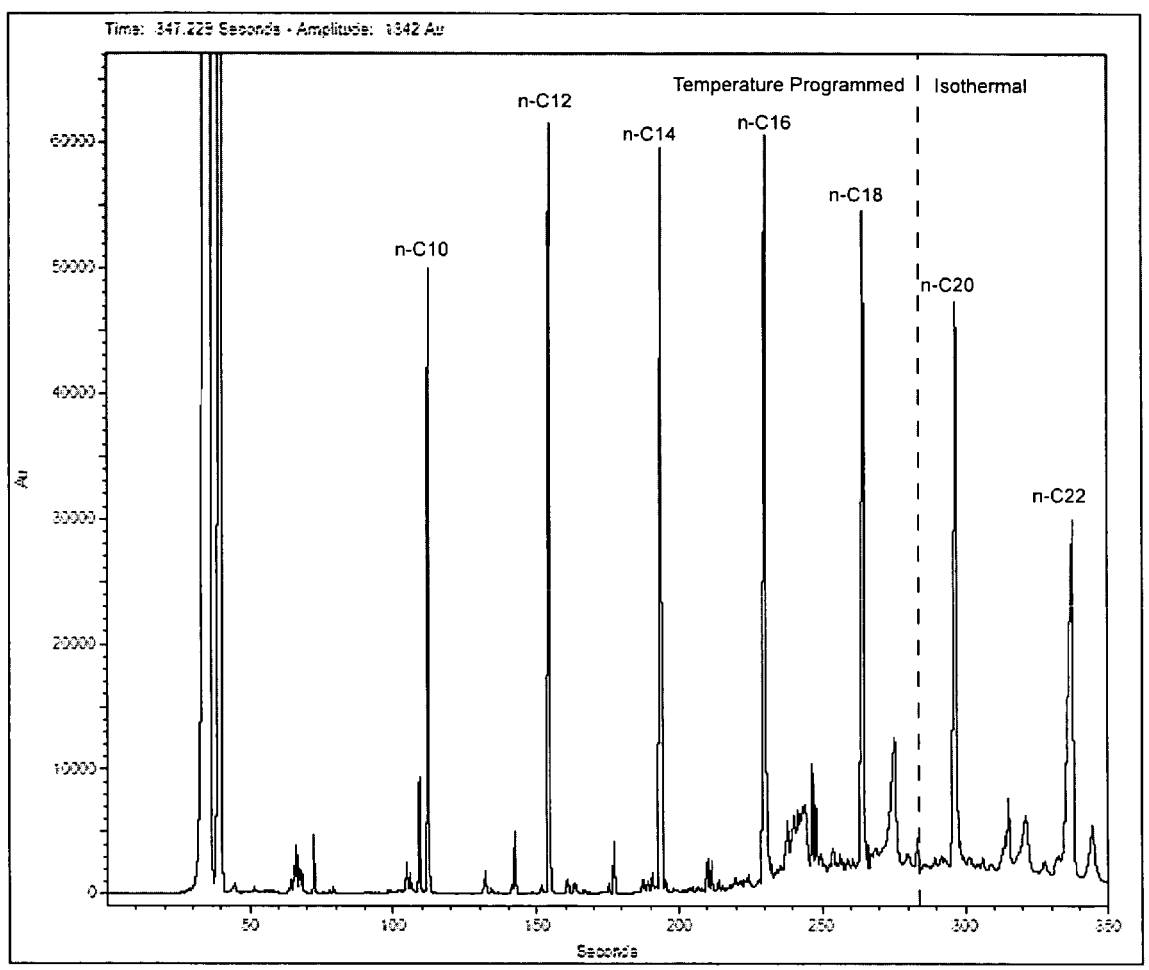
FIG. 10 is a chromatogram showing a highly efficient chemical separation of semi-volatile n-alkane hydrocarbons with a temperature program heating rate of 60 degrees C./second performed using the subject invention with a 8 meter long capillary column length.
Figure 11:
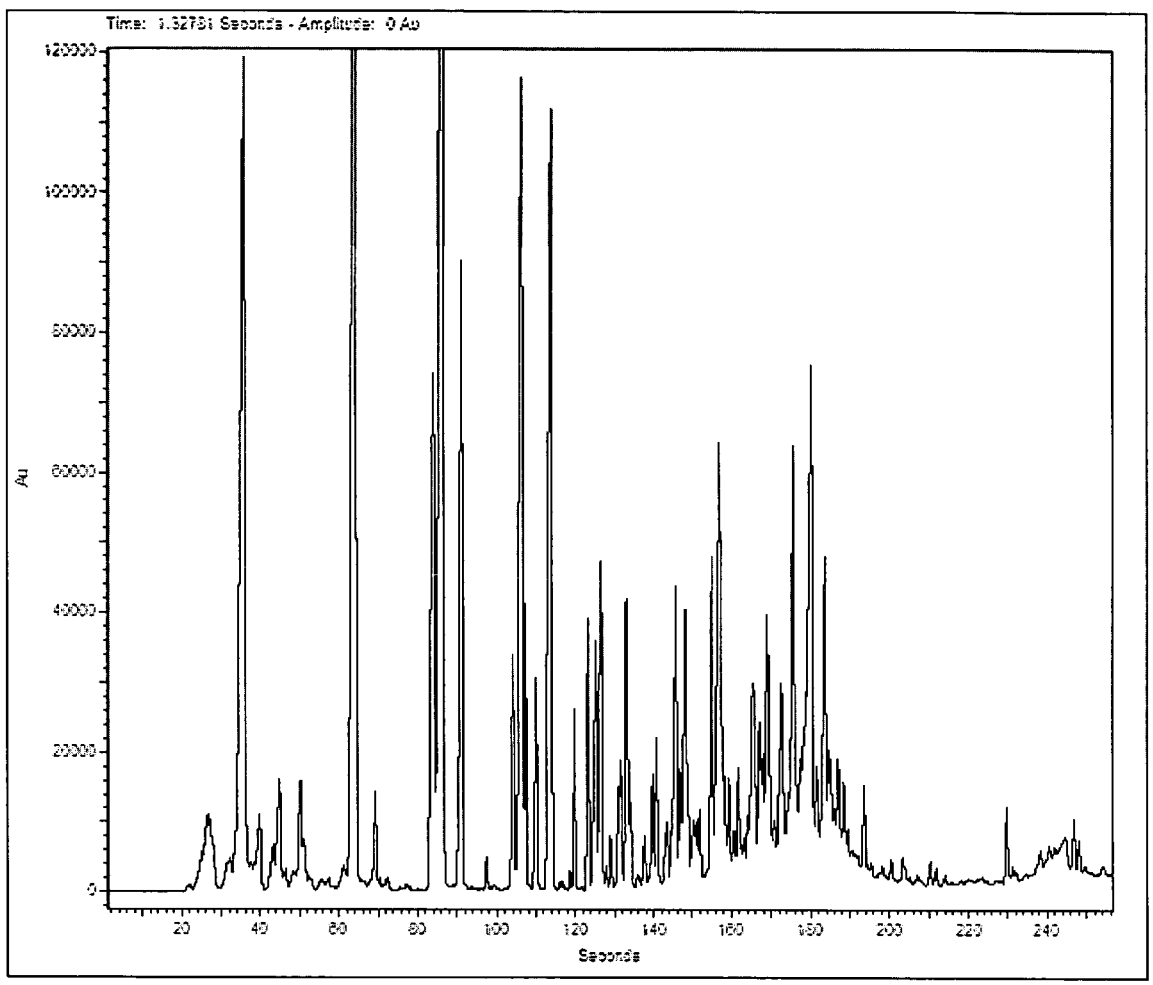
FIG. 11 is a chromatogram showing a highly efficient chemical separation of gasoline with a temperature program heating rate of 60 degrees C./second performed using the subject invention with a 8 meter long capillary column length.
Figure 12:
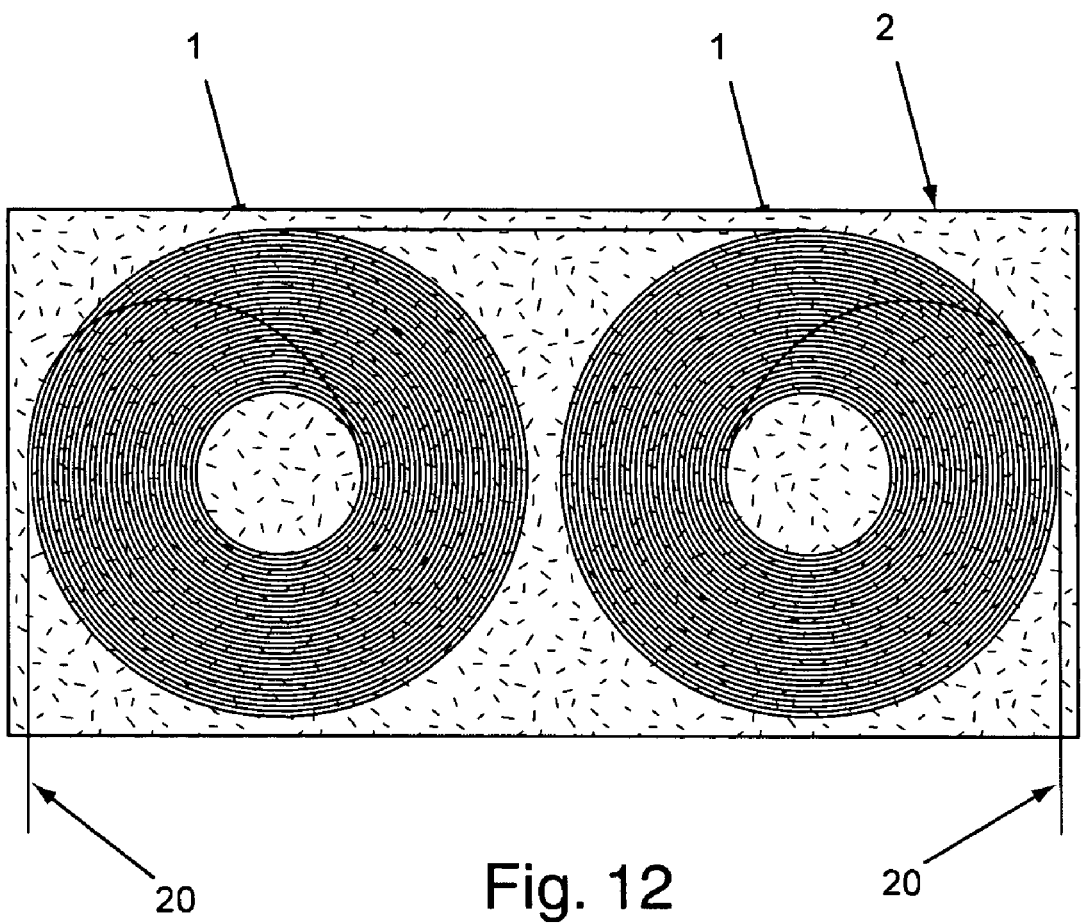
FIG. 12 is a schematic representation of a multi-sectioned capillary column assembly containing dual coils of capillary column material.
Figure 13:
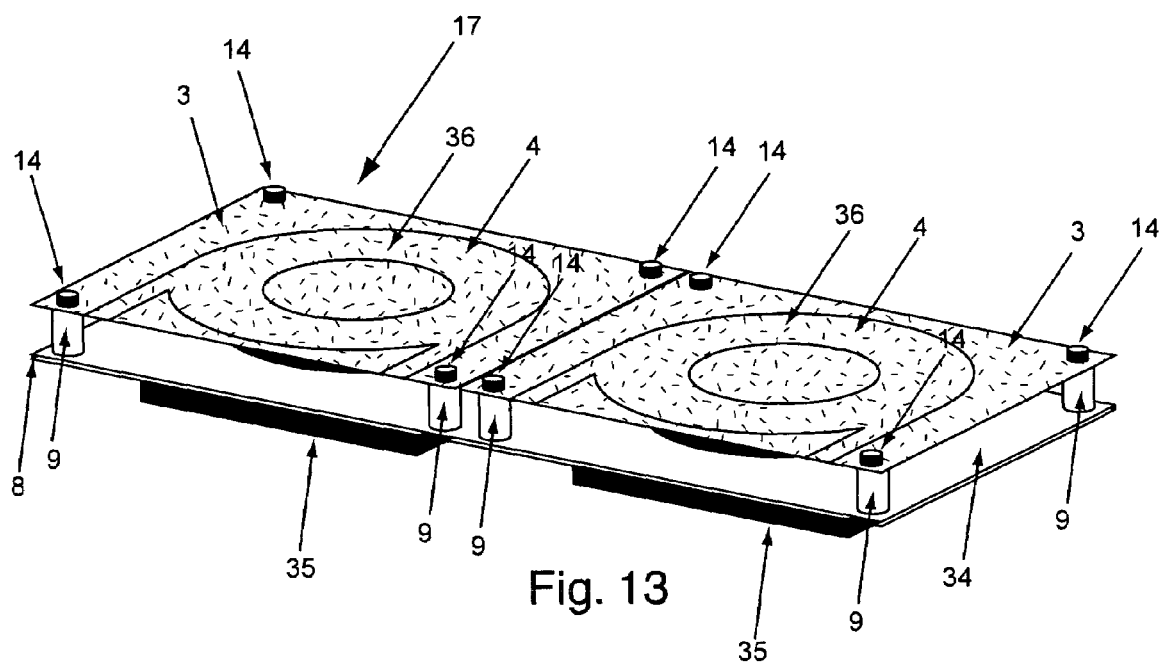
FIG. 13 is a schematic representation of a multi-sectioned thermal modulator attached to a single base surface.
Figure 14:
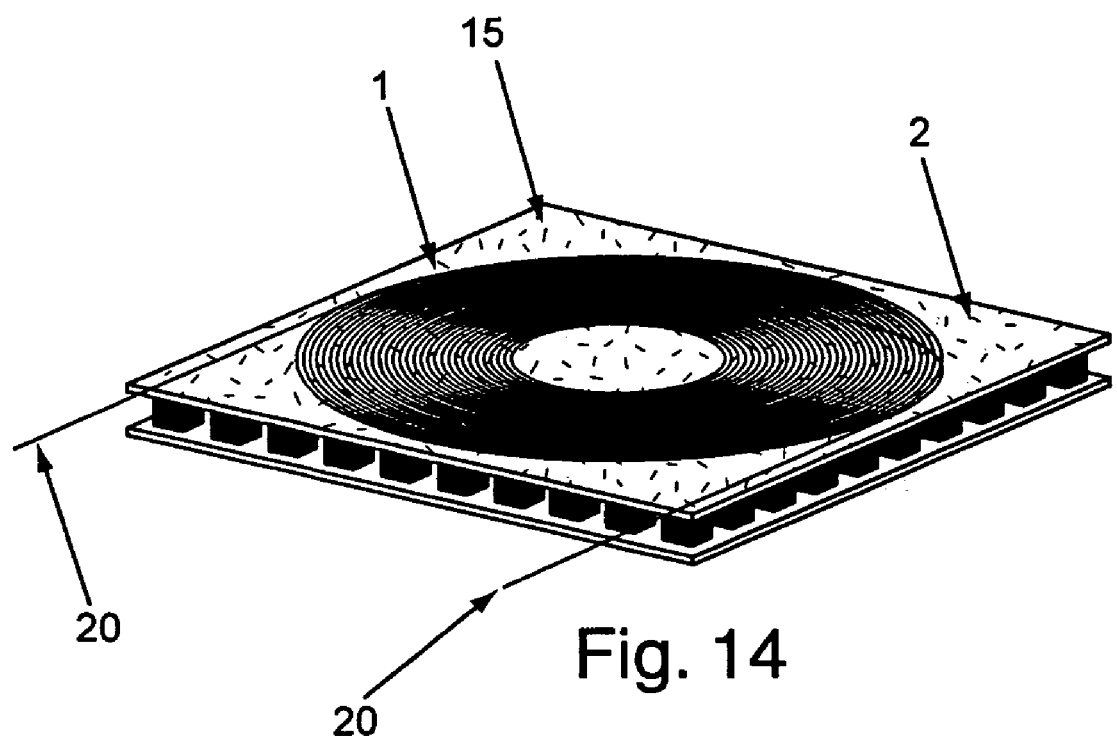
FIG. 14 is a schematic representation of a capillary column assembly attached to a Peltier thermoelectric cooler.
Figure 15:
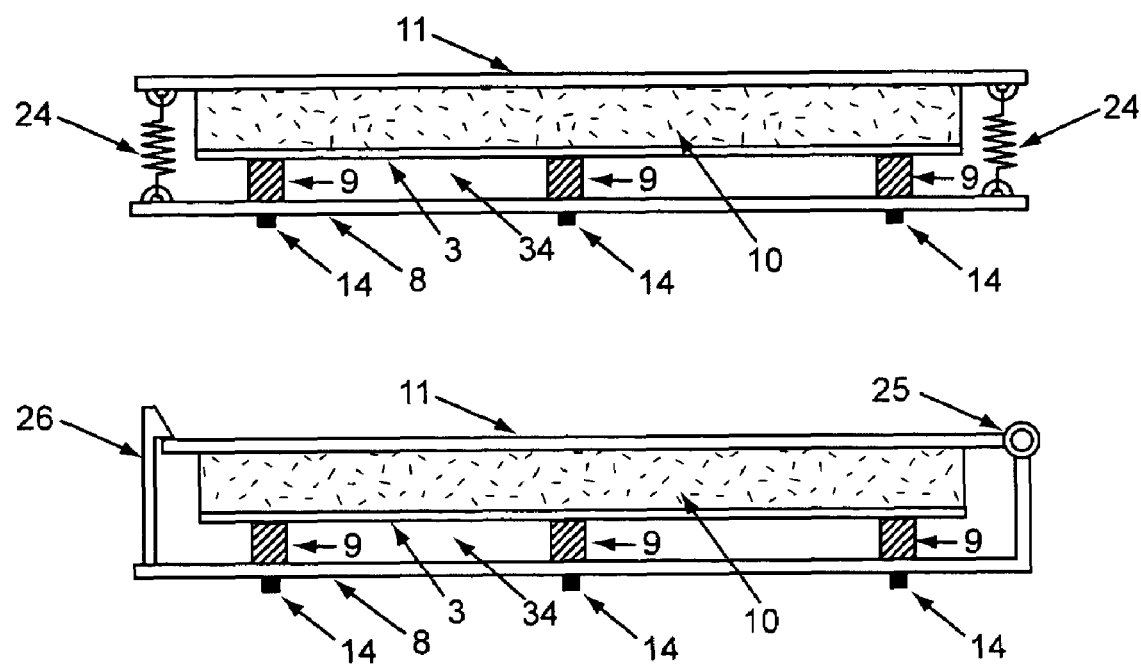
FIG. 15 is a schematic representation of thermal modulators with different mechanical compressing devices used to provide pressure to the insulating material such that the capillary column assembly is kept in intimate contact with the heater surface. The mechanical compressing devices are comprised of a set of springs and a hinged arm with a latch.

Chemical analyses were performed using the subject invention with the above described "microFAST GC". FIGS. 9-11 show the results from analyses performed. FIG. 9 is a chromatogram obtained from injecting a semi-volatile n-alkane hydrocarbon mixture with the chemical compounds labeled above each peak of interest. This analysis was performed at a fast temperature ramp rate of 300 degrees C./min using a 1.7 meter, 100 micrometer, inside diameter (i.d.) capillary column. Of particular interest is the very sharp evenly spaced nature of the chemical peaks in the temperature programmed portion of the chromatogram. This is a clear indication of a high-efficiency chemical analysis.

FIG. 10 represents the same chemical sample analyzed, but with the capillary column assembly 15 containing an 8 meter length of capillary column material 1 of 100 micrometer i.d. and temperature programmed at 60 degrees C./min. Once again, the very sharp, evenly spaced chemical peaks in the temperature programmed portion of the chromatogram are indicative of very efficient thermal transfer to the capillary column material 1, in addition, the extra resolution of the analysis can also be observed due to the longer column employed. FIG. 11 represents the same capillary column assembly 15 and conditions as the previous figure with the sample instead being pure gasoline. This is yet another display of the thermal efficiency and versatility that can be realized with the present invention that is normally confined to, and in some case, unattainable by conventional instrumentation.

What I claim is:

1. A gas chromatography capillary separation column assembly comprising;
    a coiled planar capillary separation column;
    a thermal modulator for altering the temperature of said coiled planar capillary separation column;
    means for placing said thermal modulator in close proximity to said planar capillary separation column, and
    a surface with adhesive coating to which is affixed said coiled planar capillary separation column.

2. A gas chromatography capillary separation column assembly as in claim 1 wherein said surface with adhesive coating is a thin, high temperature resistant fiberglass cloth coated with a thin layer of high-temperature resistant silicone adhesive.

3. A gas chromatography capillary separation column assembly as in claim 1 further comprising a second surface to be applied to said surface with adhesive coating, whereby said coiled planar capillary separation column is fixed between said second surface and said surface with adhesive coating.

* * * * *